United States Patent [19]

Mayer et al.

[11] Patent Number: 4,876,109

[45] Date of Patent: Oct. 24, 1989

[54] SOLUBLE COVERING FOR CARDIAC PACING ELECTRODE

[75] Inventors: David W. Mayer, Bloomington; Byron L. Gilman, Plymouth; Susan M. Walgren, Shoreview; June M. Berglund, Forest Lake, all of Minn.

[73] Assignee: Cardiac Pacemakers, Inc., St. Paul, Minn.

[21] Appl. No.: 272,912

[22] Filed: Nov. 18, 1988

Related U.S. Application Data

[62] Division of Ser. No. 37,684, Apr. 13, 1987, Pat. No. 4,827,940.

[51] Int. Cl.$^4$ .......................... A01N 1/02; B05D 1/18; B05D 3/02
[52] U.S. Cl. ........................................ 427/2; 427/435; 427/374.1
[58] Field of Search ..................... 427/2, 435, 374.1; 128/783, 784, 785, 898, 642

[56] References Cited

U.S. PATENT DOCUMENTS 3,591,482   7/1971   Leff et al. ..................... 427/435 X
4,524,087   6/1985   Engel ................................. 427/2

*Primary Examiner*—Michael Lusighan
*Attorney, Agent, or Firm*—Orrin M. Haugen; Thomas J. Nikolai; Frederick W. Niebuhr

[57] ABSTRACT

A biocompatible covering, soluble in body fluids, surrounds the fixation helix of an implantable cardiac electrode as the electrode, and its adjoining lead, are inserted intravenously to a selected cardiac chamber. The covering size and shape are selected for protection of blood vessels and other body tissues during insertion, and for exposure of the fixation element shortly after its proper positioning. The covering may be applied to the fixation element by a dip coating process, or formed separately by casting or injection molding, for later attachment to the lead distal end using an adhesive.

3 Claims, 2 Drawing Sheets

SOLUBLE COVERING FOR CARDIAC PACING ELECTRODE

This is a divisional of application Ser. No. 07/037,684, filed Apr. 13, 1987, now U.S. Pat. No. 4827,940, patented May 9, 1989.

BACKGROUND OF THE INVENTION

This invention relates to cardiac diagnostic and chronic therapeutic leads, and more particularly to fixation leads in which an electrode includes an anchoring element.

The utility of cardiac pacing leads is well recognized, both for carrying pulse stimulation signals to the heart from a pacemaker, and for monitoring heart electrical activity from outside the body. Many such leads are sufficiently flexible and small in diameter for intravenous introduction to a cardiac cavity, whereupon an electrode at the distal end of the lead is implanted into the endocardium to secure the lead. For this purpose, helical coils, barbs and other anchoring elements are provided, typically as part of the electrode.

The anchoring element must be sufficiently sharp to penetrate the endocardium and secure the electrode against becoming detached, for example due to contractions of the myocardium. During a critical period immediately after implant and prior to full fibrotic growth, usually three to twelve weeks, the anchoring element must provide substantially the entire force maintaining the electrode in its selected location. Given these requirements, it is not surprising that an effective anchoring element can become entangled in the vein, heart valve or other tissue encountered during its intravenous insertion.

The problem has given rise to numerous proposed solutions. For example, U.S. Pat. No. 3,974,834 to Kane granted Aug. 17, 1976 shows a sleeve which shrouds the sharp tip of a fixation helix, but collapses in accordion-like fashion as the helix is turned into the endocardium. In U.S. Pat. No. 4,282,885 to Bisping granted Aug. 11, 1981, a protective core is surrounded by the helix, and is movable axially relative to the helix. A wire, attached to the core, extends through the lead and can be pulled after lead insertion to withdraw the core, exposing the helix. U.S. Pat. No. 4,146,036 to Dutcher et al granted Mar. 27, 1975 discloses an extensible and retractable core surrounded by the helix.

Other solutions involve making the fixation element movable. For example, in U. S. Pat. No. 4,180,080 to Murphy granted Dec. 25, 1979, a spiral coil, normally recessed within a guide tube, can be rotated whereby it emerges beyond the tube. U.S. Pat. No. 3,844,292 to Bolduc granted Oct. 29, 1974 discloses a plunger outside of the body which, after release of two locking mechanisms, is movable to push outward a barb-like tip. A somewhat similar arrangement, involving a platinum piston movable to push a harpoon-shaped anchor beyond the end of a tubular electrode, is shown in U.S. Pat. No. 4,258,724 to Balat et al granted Mar. 31, 1981.

Such devices, while satisfactory in certain respects, are undesirable in that leads employing them must have a larger diameter. They often require additional tools, for example a stylet-type screw driver for rotating the helix. Further, such devices are often overly complex, diminishing their reliability and raising the possibility of a current leakage path between conductors of bipolar leads.

Therefore, it is an object of the present invention to provide a smooth, rounded covering for the anchoring element of a cardiac endocardial electrode to facilitate intravenous insertion of the electrode.

Another object of the invention is to provide such a covering which is soluble in body fluids, thereby to expose the anchoring element at a specified time after its initial insertion into the body.

Yet another object is to provide a simple, non-mechanical means for covering fixation mechanisms during intravenous insertion of a pacing electrode having an anchoring element, without requiring any longitudinal relative movement between the electrode and anchoring element.

SUMMARY OF THE INVENTION

To achieve these and other objects, there is provided an intravascular lead implantable inside a patient's body. The lead includes an electrode having a fixation element for effecting penetration into endocardial tissue at a selected location to secure the electrode at the selected location. The lead includes one or more flexible electrical conductors, and one or more flexible, biocompatible dielectric sheaths surrounding the conductors along substantially their entire length. A coupling means electrically and mechanically joins the electrode to a distal end of the conductor, whereby the conductor and electrode transmit electrical signals from the selected location to the lead proximal end. A biocompatible covering surrounds the fixation element and facilitates intravascular movement of the electrode. The covering is soluble in bodily fluids and has a thickness selected to allow at least a predetermined minimum time for the intravascular insertion of the lead and electrode, and for the positioning of the electrode at least proximate to the selected location, before the covering dissolves sufficiently to expose the fixation element and permit the penetration.

Mannitol, and other sugar derivatives, have been found suitable for forming the covering, which can be produced by dipping the fixation element into a beaker containing the mannitol or other covering constituent at a temperature slightly above its melting point. The fixation element is removed, cooling the element, along with a portion of material adhering to it. Alternatively, the covering can be preformed as a capsule, with a bore formed in the capsule for accommodating the fixation element. An adhesive is then used to join the covering to the electrode, with the fixation element inside the bore.

Another aspect of the present invention is an apparatus for facilitating intravascular insertion of a cardiac pacing electrode. The apparatus includes a biocompatible, non-pyrogenic covering substantially surrounding a fixation element of an electrode. The covering is soluble in bodily fluids and has a thickness selected to allow at least a predetermined time for intravascular insertion of the electrode at least proximate a selected location inside the body of the patient, before the covering dissolves sufficiently to expose the fixation element to permit penetration of the fixation element into body tissue at the selected location.

As another aspect of the invention, there is disclosed a process for coating a fixation element of a body implantable electrode, including the steps of:

(a) selecting a biocompatible, non-pyrogenic material soluble in bodily fluids and having a melting point substantially above normal ody temperature, and heating the material to a temperature slightly above its melting point;

(b) dipping a fixation element of a body implantable electrode into a solution of the material maintained at said temperature;

(c) removing the fixation element, along with an initial portion of the material adhering to the fixation element, from the solution and permitting them to cool a sufficient time for said initial portion to at least partially solidify;

(d) dipping said fixation element and initial portion into the solution for a time sufficient to permit a subsequent portion of the material to adhere to the initial portion; and (e) removing the fixation element, initial portion and subsequent portion from the solution, and permitting them to cool to an ambient temperature.

Steps (d) and (e) may be repeated until the thickness of the covering is sufficient for the desired dissolving time.

A covering in accordance with the present invention, whether preformed or applied through dip coating, forms a smooth, blunt distal tip for its associated lead, allowing an expeditious, intravenous insertion of the lead, without concern that the fixation element will snag upon, tear or otherwise damage the vein or any other tissue as it travels toward the heart. A short time after the electrode reaches the selected cardiac chamber, there is a sufficient dissolving of the covering such that the fixation element is exposed and ready to penetrate the endocardium.

Due to the many materials suitable for the covering, which include various salts and polyvinylpyrrolidone as well as the aforementioned sugar derivatives, and further due to controlling the covering thickness, a wide range of dissolving times is available, so that a particular covering can be tailored to the expected time for a particular procedure. Further refinement is provided by the preformed capsule, due to enhanced control over size, thickness and surface area of the covering.

IN THE DRAWINGS

For a better appreciation of these and other features and advantages, reference is made to the following detailed description and the drawings, in which.

DETAILED DESCRIPTION OF THE PREFERRED EMBODIMENT

Figure 1:
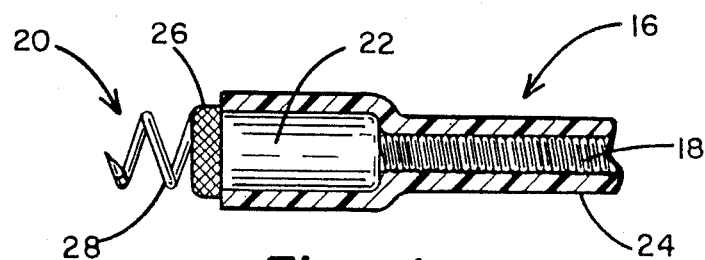
FIG. 1 is a side sectional view of the distal end region of an implantable, positive fixation, cardiac lead.

Turning now to the drawings, there is shown in FIG. 1 the distal end region of an implantable, positive fixation, cardiac lead 16. Devices such as lead 16 typically are inserted intravenously, for example into the subclavian vein or the cephalic vein, and progressively moved toward the heart until the distal end reaches a selected cardiac chamber. With the distal tip positioned at a selected location, the lead proximal end, still outside of the body, is maneuvered to implant the distal tip into the endocardium. The implanted lead transmits electrical signals between the selected location in the heart and the lead proximal end, for one or both of two purposes: to monitor heart electrical activity at the selected location, and to carry stimulating signals to the selected location from a pulse generator (not shown) connected to the lead proximal end.

To transmit the electrical signals there is provided an electrical conductor, shown in FIG. 1 as a double-wound coil 18 formed of a nickel alloy. The coil provides maximum flexibility for conforming to the vein, with minimal stress on the conductor. At the distal end of the lead is an electrode 20, electrically and mechanically coupled to coil 18 by a platinum alloy crimp tube 22. A flexible, dielectric sheath 24 surrounds the coil and crimp tube. A suitable material for the sheath is silicone rubber.

Electrode 20 is porous, having a screen 26 formed of a platinum alloy. Screen 26 aids in chronic fixation, whereby fibrous connective tissue intertwines with the screen to firmly secure electrode 20. Fibrous encapsulation, however, can take weeks, and it is essential to provide a means for positively securing the lead distal end during the time immediately following implantation. To this end, there is provided a fixation helix 28 of platinum alloy. Helix 28 has a sharp point at its distal end, which readily penetrates the endocardium. Upon initial penetration, the helix is manipulated from the proximal end of lead 16, whereby it rotates clockwise, to further penetrate the tissue, to the point of firmly securing electrode 20 at the designated endocardial location.

A problem associated with helix 28 is that its sharp tip is capable of snagging and becoming entangled with the blood vessel wall, venous valves, or heart valve. Consequently, the physician using lead 16 typically is advised to rotate the helix counterclockwise, which tends to draw the sharp point of the helix away from the tissue it encounters, to minimize the potential for entanglement. Alternatively, protective devices, such as those discussed above, have been employed.

Figure 2:
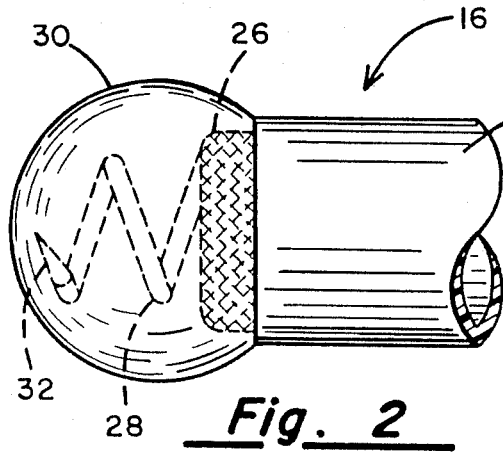
FIG. 2 is an enlarged side view showing the lead of FIG. 1 provided with a soluble coveing in accordance with the present invention.

FIG. 2 illustrates lead 16 with a covering or tip 30 mounted at its distal end in accordance with the present invention. Tip 30 is solid, and adheres to helix 28, screen 26 and the distal end of sheath 24. The outer surface of tip 30 is generally spheroid. However, the precise surface configuration is not so important as the fact that tip 30 is smooth, rounded and blunt, and that it completely surrounds fixation helix 28 to protect intravascular and other tissue from the fixation helix, particularly its sharp point 32.

Tip 30 is composed of a non-toxic, biocompatible and non-pyrogenic material. Also, the material must be soluble in body fluids (particularly blood), within a temperature range encompassing normal body temperature (37° C.). Further, the material of tip 30 must maintain its structural integrity in an environment of body fluids at or about normal body temperature, in that it should not undergo plastic or elastic deformation as it dissolves. Usually the structural integrity requirement is satisfied if the melting point of the tip is substantially above normal body temperatures, in fact preferably 60° C. or higher.

Figure 3:
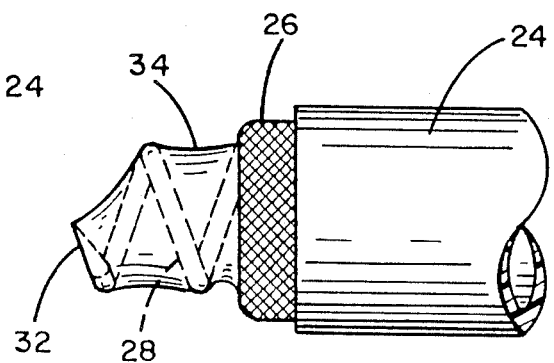
FIG. 3 is a view similar to that of FIG. 2, illustrating the covering at an intermediate stage of its formation.

In one example, tip 30 has been formed of mannitol, chemical formula $C_6H_{14}O_6$. Mannitol has a melting point of about 167° C., and one gram dissolves in about 5.5 milliliters of water, with solubility being greater in hot water. Mannitol in a glass beaker was first heated to a temperature between 177° and 182° C., slightly above its melting point, and maintained at that temperature. The distal end of lead 16 was immersed in the mannitol solution for a brief time and withdrawn. A portion of the mannitol adhered to helix 28, forming a core portion 34 as illustrated in FIG. 3. Away from the beaker, helix 28 and core portion 34 were allowed to cool a sufficient time for the core portion to solidify. This cooling required about five seconds.

Following cooling, the lead distal end was dipped into the mannitol melt once again, then withdrawn after about one second. A second portion of the mannitol melt, adhering to core portion 34, helix 28 and screen 26, was sufficient in combination with the core portion to form tip 30 as illustrated in FIG. 2. The spheroid tip configuration results from the natural surface tension of the mannitol melt as it solidifies. A tip formed in this manner dissolves in water heated to about 38° C. in about three and one-half minutes.

Repeated trials of this example have yielded consistently satisfactory lead tips. The results indicate that the precise temperature of the mannitol melt is not critical, so long as it is maintained in liquid form, slightly above the melting point. Likewise, the duration of each dip coating is not critical, although it must be sufficient for adherence of subsequent mannitol layers while not so long as to melt mannitol previously solidified onto the lead. Finally, as the number of dip coatings required is largely a function of desired tip size, certain tip designs may require substantially more than the two dip coatings described.

The dissolving time for tip 30 in body fluid is controlled principally by the tip material, surface area and thickness so that increased dissolving times can be provided, if desired, by increasing the tip thickness. The main concern is that tip 30 be of sufficient size to ensure that lead 16 can be directed intravenously to the selected cardiac chamber prior to exposure of helix 28, particularly at point 32. Also of concern is that within a reasonably short time after insertion, tip 30 is completely dissolved to expose helix 28 for the implanting of electrode 20.

While the above example involves mannitol, other sugar derivatives stable at temperatures below 60° C. are suitable substitutes, for example dextrose, sorbose, sucrose, and glucosamine. Also usable are certain salts, for example sodium chloride, potassium chloride and sodium carbonate. A further suitable constituent is polyvinylpyrrolidone (PVP). These materials are suitable, as well, with non-helical fixation elements.

Figure 4:
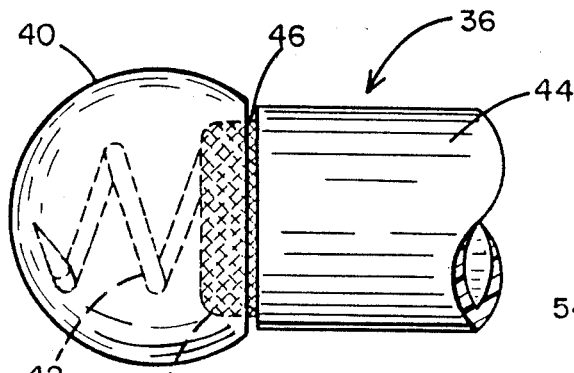
FIG. 4 is a side view of a lead provided with a second embodiment covering.
Figure 5:
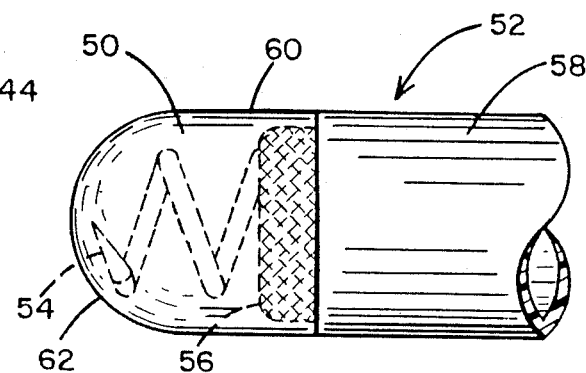
FIG. 5 is a side elevation of a lead provided with a third embodiment covering comprising a molded tip.

The dip process described above, when used to form tip 30, tends to trap air which expands due to heating, and can cause undesirable formation of bubbles in the tip. In such cases, it is advantageous to control the degree to which the lead distal end is submerged into the constituent melt. For example, FIG. 4 illustrates a lead 36 in which a tip 40 entirely surrounds a fixation helix 42. Tip 40 does not abut a sheath 44, but leaves a proximal portion 46 of a screen 48 exposed. As a result of such controlled submersion, air can escape through proximal portion 46, and later the proximal portion facilitates ethylene oxide sterilization of the lead distal end.

For improved control over the size and shape of the soluble tip, a tip 50 for a lead 52 is formed by a casting or injection molding of a constituent melt. The tip surrounds a helix 54 and screen 56, to abut a sheath 58. As indicated at 60, the profile of the tip along its side is linear, while a rounded blunt distal end 62 is retained. This allows a reduction of tip diameter to the nominal lead diameter, to further facilitate intravenous insertion.

Figure 6:
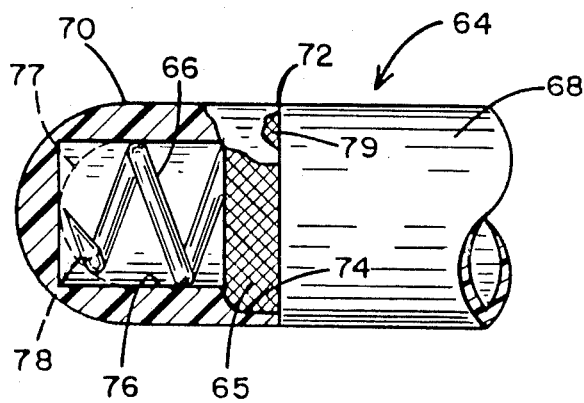
FIGS. 6 and 7 are side views of leads provided with coverings comprising pre-molded tips.

Another method of controlling the size and shape of the tip is to preform the tip by casting or injection molding. FIG. 6 illustrates a lead 64 with a screen 65 and fixation helix 66 affixed to a conductor which is surrounded by a sheath 68. Surrounding the helix and screen is a preformed tip or capsule 70, fixed to sheath 68 using an adhesive at 72. Such adhesive can be the molten material itself in the case of mannitol, a heated syrup of fructose and sucrose which solidifies upon cooling, or syrups of other sugars (mannitol, sorbitol, etc.). A large diameter opening 74 is formed in capsule 70 to accommodate screen 65, while a cylindrical bore 76 of greater depth accommodates helix 66. As indicated by broken lines at 77 and 78, bore 76 can be shaped to provide a substantially uniform thickness in capsule 70 if desired. One or more openings, as indicated at 79, can be formed if desired to facilitate sterilization and increase the capsule surface area exposed to bodily fluids during lead insertion.

Although it requires an adhesive not needed in the dip coating or direct mold approach, a preformed tip has several significant advantages. First, it affords maximum control over the tip size and shape, so that a comparatively precise dissolving time can be achieved by appropriately selecting tip constituents and tip thickness. The resulting consistency among many tips renders the preformed tip the preferred choice for mass production. Also, the preformed tip requires less of the tip constituent. In particular, no constituent is provided where none is needed—namely, in the cylinder defined by the fixation helix. This factor contributes to more predictable dissolving times as well as material savings. Preformed tips are more amenable to being installed or replaced on site. Finally, constituents that cannot be melted because of their thermal instability, but which have the desired dissolving properties, can be formed into a tip such as tip 70 by compression or molding. Examples of such constituents are lactose, lecithin in combination with other materials, and glucosamine.

Figure 7:
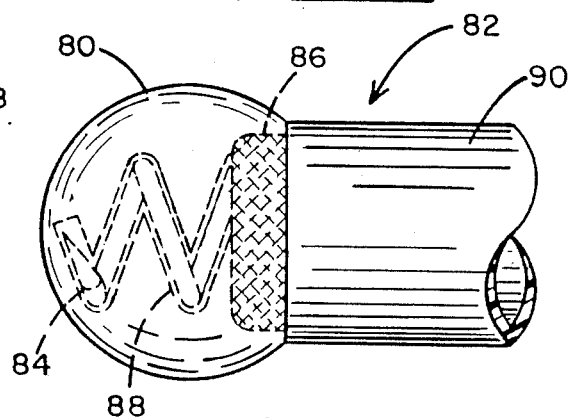

In FIG. 7, an alternative preformed tip or capsule 80 is mounted to a lead 82 over its fixation helix 84 and screen 86. A helical bore 88 is formed in tip 80, of a size and shape to accommodate helix 84, so that tip 80 is secured to lead 82 by turning it clockwise upon the helix. So mounted, tip 80 depends less upon an adhesive, and may not require any adhesive to connect it to a sheath 90.

Figure 8:
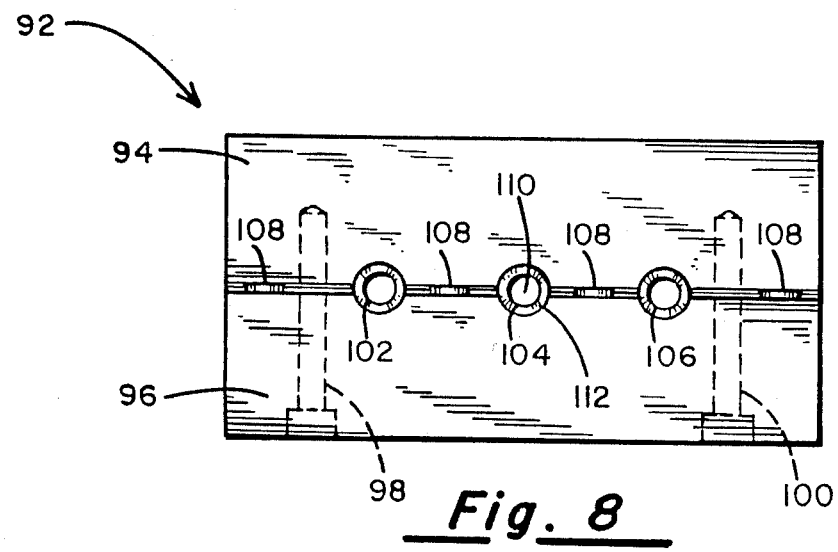
FIGS. 8 and 9 are top and side views, respectively, of a tool used in forming soluble coverings pursuant to the present invention.
Figure 9:
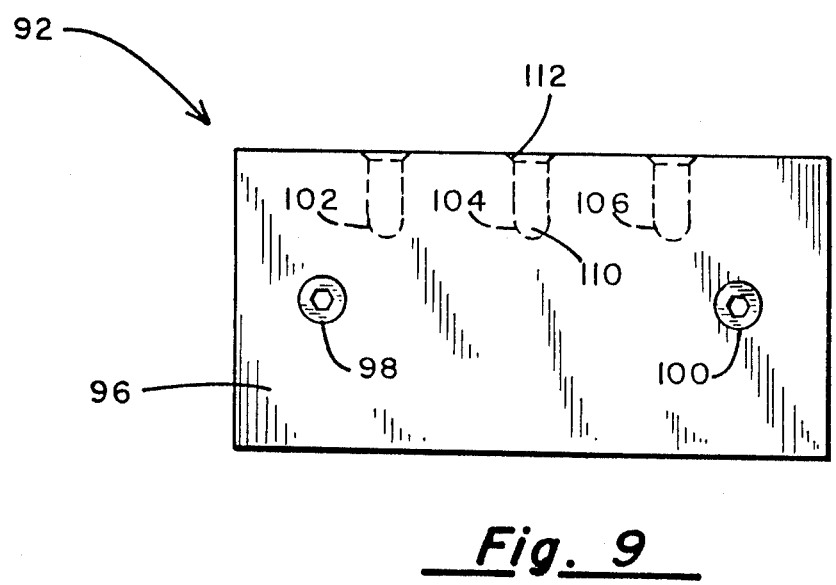

Shown in FIGS. 8 and 9 is a forming tool 92, which is an aluminum block including two opposed sections 94 and 96 held together by socket head screws 98 and 100. The opposing walls of sections 94 and 96 are cut away to form cavities 102, 104 and 106 when sections 94 and 96 are mounted with respect to each other as shown in the figures. Spacers, indicated at 108, maintain a slight gap between sections 94 and 96, preferably of about 0.005 inches.

The cavities are substantially identical in shape, although they can be formed in different sizes corresponding to tips of different selected sizes. Cavity 104, for example, includes a tip forming segment 110 and an upper chamfered segment 112. Tip forming segment 110 has the desired cylindrical sides and rounded base to form the desired blunt tip, while chamfered segment 112 facilitates insertion of tips prior to their shaping, and also serves as a temporary catch basin for excess melted tip material.

Forming tool 92 is used to control the size and shape of a soluble tip formed by the dip process described in connection with FIGS. 2-4. More particularly, the lead distal end is dipped in the mannitol solution, permitted to cool, then dipped again, this process being repeated a sufficient number of times to form a tip larger than the desired size. Then, after heating forming tool 92 to a desired temperature, preferably slightly over the mannitol melting point, the tip formed by dip coating is momentarily inserted into the desired one of cavities 102-106, then quickly withdrawn, the desired time within the chosen cavity being a fraction of a second. During this brief insertion, the heated cavity wall melts the excess mannitol, whereupon the melt is removed by draining through the gap formed by spaces 108. Part of the excess mannitol melt is collected briefly in chamfered segment 112 before drainage. While not necessary, the tip can be rotated slightly about a vertical axis while inserted, to further ensure the desired cylindrical sides and blunt end.

Whether formed by dip coating, direct molding or molded separately for later attachment, a soluble tip in accordance with the present invention renders cardiac pacing lead implantation safer and less traumatic to the patient. As it is moved toward the heart through a selected vein, the tip dissolves, but at a sufficiently slow rate to prevent exposure of the fixation helix or other fixation element, until the electrode is at least near to its selected location along the endocardium. The smooth, rounded and blunt tip in fact expedites intravascular lead insertion. The tip thickness and constituent can be selected in accordance with the anticipated insertion time, with particular accuracy in the case of a preformed tip or capsule. Thus, within a brief period of time after proper positioning, the fixation helix or other fixation element can be manipulated from outside the body, in the usual manner, to secure the electrode.

What is claimed is:
1. A process for coating a fixation element of a body implantable electrode, including the steps of:
    (a) selecting a biocompatible, non-pyrogenic material soluble in bodily fluids and having a melting point substantially above normal body temperature, and heating said material to a temperature slightly above its melting point;
    (b) dipping a fixation element of a body implantable electrode into a solution of said material maintained at said temperature;
    (c) removing said fixation member, along with an initial portion of said material adhering to said fixation member, from said solution and permitting them to cool a sufficient time to allow said first portion to at least partially solidify;
    (d) dipping said fixation member and material portion, after said cooling, into said solution for a time sufficient to permit a subsequent portion of said material to adhere to said initial portion; and
    (e) removing said fixation member, initial portion and subsequent portion from said solution, and permitting them to cool to an ambient temperature.
2. The process of claim 1 including the further steps of:
    repeating steps (d) and (e) until the combined thickness of said initial portion and all subsequent portions is at least a predetermined value.
3. The process of claim 1 including the further steps of:
    providing means defining a cavity having a selected size and shape, and heating a wall forming said cavity to a preselected temperature at least as high as the melting point of said material; and
    with the combined thickness of said material portions being at least said predetermined value to form a tip larger than said cavity, momentarily inserting said tip into said cavity to melt excess material; and draining said excess material from said cavity.

* * * * *